Figure 1:
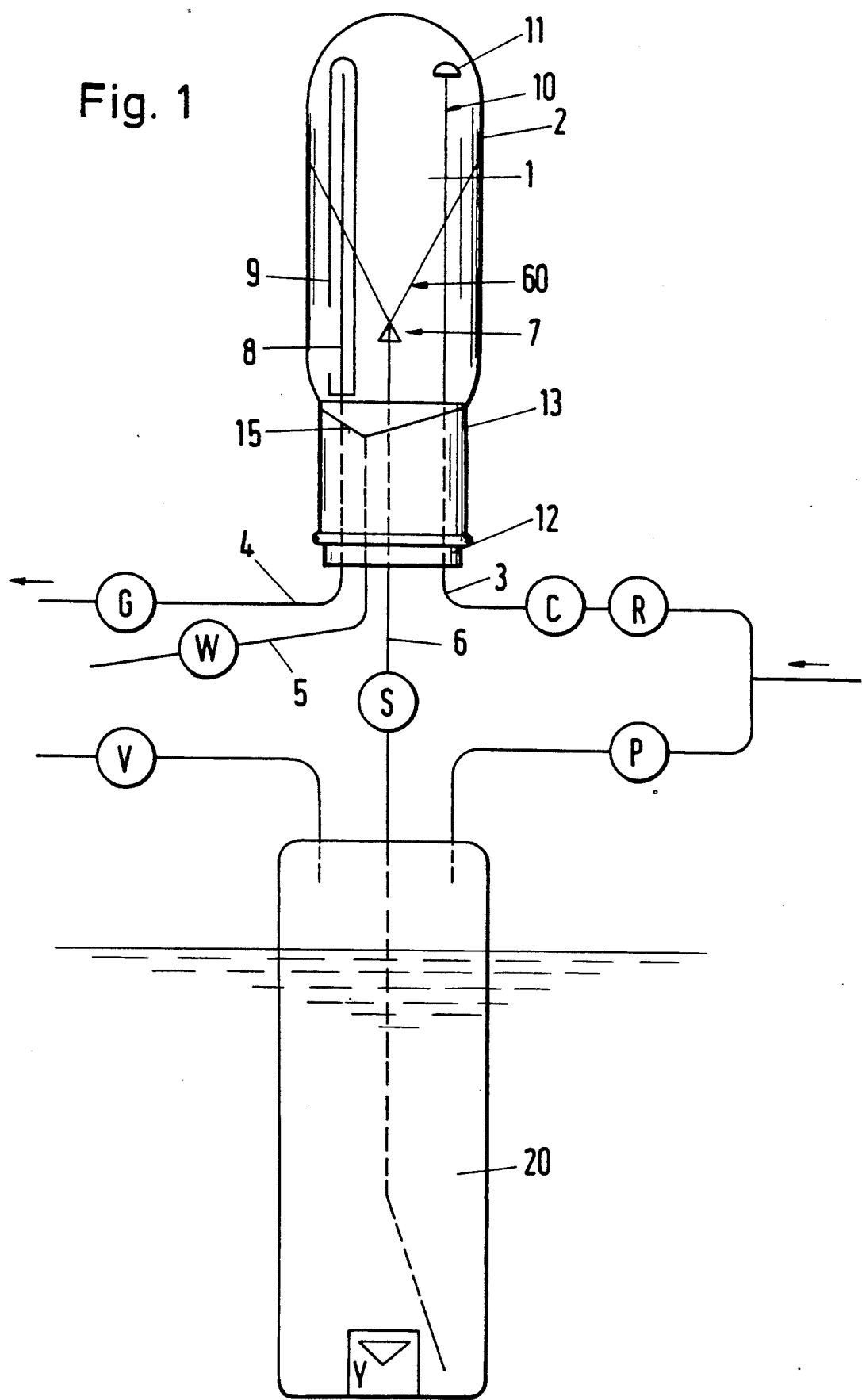

United States Patent [19]

Baykut

[11] Patent Number: 5,258,057
[45] Date of Patent: Nov. 2, 1993

[54] METHOD AND APPARATUS FOR EXTRACTING DISSOLVED, VOLATILE SUBSTANCES FROM LIQUIDS INTO THE VAPOR PHASE

[75] Inventor: Goekhan Baykut, Bremen, Fed. Rep. of Germany

[73] Assignee: Bruker-Franzen Analytik GmbH, Fed. Rep. of Germany

[21] Appl. No.: 978,078

[22] Filed: Nov. 18, 1992

Related U.S. Application Data

[63] Continuation of Ser. No. 724,879, Jul. 2, 1991, abandoned.

[30] Foreign Application Priority Data

Jul. 2, 1990 [DE] Fed. Rep. of Germany ....... 4021239

[51] Int. Cl.$^5$ .................................................. B01D 15/08
[52] U.S. Cl. .......................................... 95/89; 95/263; 96/105; 96/203
[58] Field of Search ................. 55/53, 67, 196, 197, 55/240, 386

[56] References Cited

U.S. PATENT DOCUMENTS

| | | | |
|---|---|---|---|
| 2,869,674 | 1/1959 | Vandenburgh | 55/196 X |
| 2,908,652 | 10/1959 | Forrester | 55/53 X |
| 3,070,935 | 1/1963 | DeLeon | 55/196 X |
| 3,491,512 | 1/1970 | Timmins et al. | 55/197 X |
| 3,626,761 | 12/1971 | Haruki et al. | 55/197 X |
| 3,653,182 | 4/1972 | Welch | 55/53 |
| 3,733,789 | 5/1973 | Rebours | 55/240 X |
| 3,920,420 | 11/1975 | Valentin et al. | 55/197 X |
| 4,266,950 | 5/1981 | Makino et al. | 55/196 |
| 4,316,728 | 2/1982 | Caesar | 55/240 X |
| 4,374,656 | 2/1983 | Schrenker et al. | 55/196 X |
| 4,699,886 | 10/1987 | Lelong | 55/53 X |
| 4,927,433 | 5/1990 | Wieland et al. | 55/53 X |
| 4,954,147 | 9/1990 | Galgon | 55/53 |

FOREIGN PATENT DOCUMENTS 0835461 6/1981 U.S.S.R. ............................. 55/196

OTHER PUBLICATIONS

Analysis 1987, v. 15, No. 10, pp. 560–563, "Utilization of Spray Technique in an Isolation Unit for Organic Compounds", M. Biziuk et al.

Intern. J. Environ. Anal. Chem. 1986, vol. 26, pp. 193–207, "Simple Device for Isolation of Organic Compounds from Water", M. Biziuk et al.

Rev. Sci. Instrum. 63(5), May 1992, pp. 3196–3200, "Spray Extractor: A New Sampling Device for Gas Chromatographic/Mass Spectrometric Analysis of Volatile Organic Compounds in Aqueous Systems", G. Baykut.

"Feldmessung von Emission und Deposition Atmosphaerischer Spurengase im Boden und Wasser", Spurengasanalytik Suppl. Mar. 1985, pp. 74–78.

"Continuous Monitoring of Volatile Hydrocarbons in Water at the ppb Level", International Laboratory, Sep. 1989, pp. 16–20.

Analytical Chemistry, vol. 64, No. 6, Mar. 15, 1992, pp. 677–681, "Spray Extraction of Volatile Organic Compounds from Aqueous Systems into the Gas Phase of Gas Chromatography/Mass Spectrometry", G. Baykut et al.

*Primary Examiner*—Robert Spitzer
*Attorney, Agent, or Firm*—Hill, Steadman & Simpson

[57] ABSTRACT

In a method for extracting volatile substances from a vaporized liquid in which the vaporized liquid is withdrawn from an extraction chamber, a method of producing the vaporized liquid. The method includes the steps of introducing a carrier gas into the extraction chamber to form a vapor space, and spraying a liquid into the vapor space to form a vaporized liquid. An apparatus for practicing the method includes an extraction chamber in fluid communication with a liquid specimen source, and a liquid injection arrangement extending into the extraction chamber for spraying the liquid from the liquid specimen source in the vapor space to form a vaporized liquid. A carrier gas supply arrangement is provided adjacent to the extraction chamber for introducing carrier gas into the chamber to form a vapor space. The apparatus may further include a specimen chamber for collecting a predetermined amount of liquid prior to spraying.

19 Claims, 17 Drawing Sheets

METHOD AND APPARATUS FOR EXTRACTING DISSOLVED, VOLATILE SUBSTANCES FROM LIQUIDS INTO THE VAPOR PHASE

This is a continuation of application Ser. No. 724,879, filed Jul. 2, 1991, now abandoned.

TECHNICAL FIELD

The invention is directed to a method for extracting dissolved, volatile substances from vaporized liquids, whereby the vaporized liquids are withdrawn from a vapor space, and to an apparatus for implementation of the method.

BACKGROUND OF THE INVENTION

The analysis of dissolved or dispersed chemicals in water can be implemented with the assistance of gas-chromatographic vapor space analysis. In this method, the specimen is brought into a gas-liquid distribution equilibrium with a carrier gas in a vapor space. After reaching equilibrium, the specimen is withdrawn from the vapor space and gas-chromatographically analyzed. In such known extraction techniques, the vaporized liquid in the vapor space is replaced with a carrier gas after taking the specimen. Introduction of the carrier gas disturbs the equilibrium that had previously been established. Equilibrium is subsequently re-established, and a second specimen is taken. This procedure is repeated several times in order to determine the respective concentration values of the gaseous specimens. The quantity of substances contained in the specimen can be derived from the relationships between the identified concentration values. This technique provides relatively precise measurements for substances having a high fugacity.

In order to ensure the accuracy of such known methods, the gas-liquid distribution equilibrium must be attained, or "set", as quickly as possible. Short setting times are achieved when the contact surface between the liquid and the carrier gas is extremely large. In one known method, the contact surface is kept as large as possible by continuously bubbling a gas stream through the liquid. Such a method is also known from the article "Feldmessung von Emission und Deposition Atmosphaerischer Spurengase im Boden und Wasser", Spurengasanalytik Suppl. 3/85, pages 74-78, and from the article "Continuous Monitoring of Volatile Hydrocarbons in Water at the ppb Level", International Laboratory, September 1989, pages 16-20. The gas bubbles or gas effervescence introduced into the liquid can present a large contact surface to the liquid, provided that the diameter of the individual bubbles can be kept small and that there are a large number of such small-diameter bubbles. When rising in the liquid, the volatile constituents are collected in the gas bubbles. The specimens that are taken are usually pre-concentrated in a collector arrangement, desorbed, and then ultimately supplied for further analysis.

Extraction with gas bubbles can be continuously or discontinuously implemented. However, known methods are limited to liquid specimens that contain no tensides or frothing agents that tend to cause the liquid to foam. When foam enters into the vapor space, the entire extraction apparatus becomes unusable. A considerable portion of industrial waste waters contains such surface-active compounds. These types of contaminated liquid can not be treated with the known method and apparatus. The known method is also unsuitable for analyzing slurries, since the particles dispersed therein are potentially difficult to absorb into the gas bubbles. The contact between the various parts of the slurry and the gas bubbles that rise freely and slowly (according to the Archimedean principle) can be deficient for purely mechanical reasons. An increase in the gas pressure cannot compensate for such deficiencies; on the contrary, increased pressure causes the small gas bubbles to fuse together; thus forming larger gas bubbles. The larger bubbles rise slowly, and reduce the overall contact surface of the gas, thus further reducing the transfer rate of the substances to be removed for analysis.

SUMMARY OF THE INVENTION

It is therefore an object of the invention to provide a method for extracting dissolved, volatile substances from vaporized liquids. It is another object of the invention to provide an apparatus implementing the method, with which foaming liquids and slurries can also be treated.

These and other objects are achieved by providing, in a method for extracting volatile substances from a vaporized liquid in which the vaporized liquid is withdrawn from the vapor chamber, a method of producing the vaporized liquid. The method includes the steps of introducing a carrier gas into the extraction chamber to form a vapor space, and spraying a liquid into the vapor space to form a vaporized liquid.

The liquid may be pressurized, for example with a pressurized gas, before it is sprayed into the extraction chamber. A predetermined amount of liquid may be collected in a specimen chamber before the step of spraying. Liquid within the extraction chamber should be maintained at a level below the vapor space.

The invention also includes an apparatus for extracting volatile substances from a vaporized liquid. The apparatus includes an extraction chamber in fluid communication with the liquid specimen source, and a liquid injection arrangement, extending into the extraction chamber, for spraying liquid from the liquid specimen source in the vapor space to form a vaporized liquid. A carrier gas supply arrangement may be provided adjacent to the extraction chamber for introducing carrier gas into the extraction chamber to form a vapor space. The liquid injection arrangement may be provided as an injection valve, a nozzle, or a gas jet atomizer assembly.

The liquid injection arrangement may be configured as an injection valve capable of generating a conical spray jacket. The injection valve includes a springbiased mechanism for varying the spray aperture of the spray jacket.

The apparatus may further include a specimen chamber for collecting liquid.

The extraction chamber itself may take various forms. For example, the extraction chamber may be configured cylindrically, or with an outer wall having a wave-shaped profile, or as a generally helical tube.

A deflecting arrangement may be disposed within the extraction chamber for atomizing liquid sprayed from the liquid injection arrangement. It is contemplated that the deflecting arrangement could be configured in various ways, for example as a rod or as a rotatable deflector.

A carrier gas supply arrangement may be provided adjacent to the extraction chamber. In an exemplary embodiment, the carrier gas supply arrangement can include a carrier gas supplied to and in communication with a carrier gas source. The carrier gas supply tube extends in the extraction chamber, and has a terminal end disposed therein. A protective cap may be provided on the terminal end of the carrier gas supply tube to prevent liquid contamination of the carrier gas.

A gas discharge supply arrangement may be provided adjacent the extraction chamber for facilitating the removal of vaporized liquid and carrier gas from the vapor space. In an exemplary embodiment, the gas discharge arrangement may include a gas discharge tube extendign into the extraction chamber, with a protective sheath surrounding the gas discharge tube. The protective sheath covers the top of the gas discharge tube and extends to the floor of the extraction chamber, and has a lateral opening at a lower end thereof.

In the method of the present invention, liquid containing the substance or substances to be extracted is sprayed into the vapor space. As a result of the spraying, the contact surface area between liquid and gas is increased, so that distribution equilibrium is established in a shorter time. In contrast to known methods, in which the gas bubbles were the dynamic component, the present invention uses the sprayed liquid as the dynamic component. This reversal of dynamic and static components leads to the formation of larger surface regions for extraction, so that the method is suitable for use with foaming waste waters and slurries. As a result of the extremely small radii of curvature of the sprayed droplets of liquid, vapor pressure is increased, thereby promoting the transfer of the constituents dissolved in the liquid droplets into the carrier gas.

The method can be discontinuously or "batch" operated by collecting a predetermined quantity of liquid before the liquid is sprayed.

The method of the invention can be implemented with an apparatus that includes an extraction chamber that has a specimen admission, a liquid discharge, and an outlet for taking samples. A liquid injection arrangement is provided that receives liquid from the speciment admission, and which sprays liquid into the extraction chamber to form a vaporized liquid.

The injection arrangement can be configured in various ways, for example, as an injection valve or a nozzle. The shape of the liquid jet can be selected to suit various liquids, dependent on the selection of the nozzle.

For discontinuous or batch operation, a speciment chamber can be provided in which the liquid is first collected before it is sprayed into the extraction chamber. Liquid flow from the specimen chamber can be controlled with a magnetic shut-off valve.

In an exemplary embodiment, the extraction chamber can be composed of a glass or metal cylinder into which the liquid is sprayed such that it strikes the inside walls of the cylinder and, dependent on the speed of the liquid droplets, impinges against the inside walls, or drips down along the inside walls as a thin liquid film. In both instances, an adequately large contact surface between liquid and gas is formed, so that diffusion processes can proceed rapidly, thus establishing equilibrium in shorter times than hitherto possible.

In order to promote the break-up of the liquid jet, appropriate deflection devices can also be provided in the extraction chamber. Such deflection devices can take the form of a rod whose end face is impinged by the liquid jet, or a motor-driven rotatable deflector that can be provided with lamellae or the like, so that the liquid jet is broken into a mist of super-fine droplets.

The liquid running down along the inside walls is conducted out of the extraction chamber via a liquid discharge. It is preferable that a predetermined liquid level always be maintained above the liquid discharge opening, so that no gas can escape.

Other objects and advantages of the present invention will be apparent upon reference to the accompanying description when taken in conjunction with the following drawings.

BRIEF DESCRIPTION OF THE DRAWINGS

FIG. 1 illustrates a schematic view of an apparatus embodying the principles of the invention;

FIG. 1*a* illustrates a schematic view of an alternative embodiment of an apparatus embodying the principles of the invention;

FIG. 2 illustrates a control diagram for a valve arrangement corresponding to the apparatus of FIG. 1;

FIG. 3 illustrates an embodiment of an extraction chamber;

FIG. 4 illustrates a perspective view of the admissions and discharges for liquid and carrier gas on a closure plug for the extraction chamber of FIG. 3;

FIG. 5 illustrates a partially broken-away view of the arrangement of FIG. 4;

FIG. 6 schematically illustrates a partially broken-away view of the pressure valve of FIG. 6;

FIG. 6*a* schematically illustrates a detailed view of the pressure valve of FIG. 6;

FIG. 7*a* illustrates an exemplary embodiment of an extraction chamber in operation;

FIG. 7*b* illustrates a further exemplary embodiment of an extraction chamber having a deflection arrangement;

FIG. 7*c* illustrates an embodiment of an extraction chamber having a rotatable deflector;

FIG. 8 illustrates an extraction chamber wherein the liquid jet is introduced at low speed;

FIG. 9 illustrates an extraction chamber wherein the walls have a wave-shaped profile;

FIG. 10 illustrates an extraction chamber in the form of a generally helical tube;

FIG. 11 illustrates an extraction chamber including a gas nozzle having a spraying direction perpendicular to the spraying direction of the liquid nozzle;

FIG. 12 illustrates an extraction chamber wherein the liquid is introduced in conjunction with compressed gas; and FIG. 13 illustrates an extraction chamber wherein liquid is sprayed into the vapor space through an injection valve.

DESCRIPTION OF THE PREFERRED EMBODIMENT

FIG. 1 illustrates a schematic, overall view of an apparatus embodying the principles of the present invention. The apparatus includes an extraction chamber 1, a specimen chamber 20, and a valve system C, G, P, R, S, V, W. The valve system is actuated by an appropriate control system, for example by a computer. A pressure valve Y is provided at the underside of the specimen chamber 20. The liquid to be treated can enter into the specimen chamber 20 through the pressure valve Y. When the specimen chamber 20 has been filled to a desired level, gas under pressure is delivered into the specimen chamber 20 via the control valve P. The pressure closes the valve Y, thus preventing further admission of liquid into the chamber 20. Further admission of pressure into the specimen chamber 20 causes liquid to proceed into the extraction chamber 1 via the specimen space valve S. The valve S can, for example, be a magnetic shut-off valve. The specimen chamber 20 may be refilled by interrupting the influx of pressurized gas, and relieving the pressure in the specimen space 20 via the pressure relief valve V. The pressure relief valve V and the compressed gas valve P communicate with the interior of the chamber 20 via conduits that pass through the upper wall of the specimen chamber 20. The magnetic shut-off valve S in the transition line between the specimen chamber 20 and the extraction chamber 1 makes it possible to almost instantaneously interrupt the introduction of liquid into the extraction chamber 1. The extraction chamber 1 is essentially cylindrical. A neck 13 is formed on the underside of the chamber 1, and is adapted to accept a plug 12 with which the chamber is closed. The requisite gas and liquid conduits are conducted through the plug 12. Carrier gas is introduced into the chamber 1 via a pressure-reducing valve R, a carrier gas admission valve C, and a gas delivery conduit 3. The gas delivery conduit 3 discharges into an admission tube 10 provided with a protective cap 11. The admission tube 10 extends through the plug 12 into the inside of the cylinder 2. A liquid conduit 6 similarly extends through the plug 12, and discharges into a liquid injection arrangement 7 with which the liquid is sprayed. The design of the nozzle may be selected to provide a jet 60 that is fanned to varying degrees. Specimens are removed from the extraction chamber via a vapor discharge 4. The discharge 4 is in communication with a gas discharge pipe 8 that passes through the plug 12 into the inside of the cylinder 2. The discharge pipe 8 is provided with a protective sheath 9 that substantially prevents liquid droplets from entering the discharge tube 8. The vapor to be removed reaches the discharge pipe 8 through an opening 92 provided in the protective sheath 9. A sump 15 is provided at the lower end of the chamber 1. A liquid discharge conduit 5 is provided at the bottom of the sump 15, and passes through the plug 12 at a side thereof adjacent the inside of the cylinder 2. The liquid situated in the inside of the cylinder 2 can be discharged via a liquid discharge valve W. During operation of the apparatus, it is essential that liquid be maintained at a predetermined level to prevent vapor from escaping through the liquid discharge conduit 5.

In certain situations, for example in a continuous extraction method, liquid can alternatively be pumped into the extraction chamber. It is also possible to employ a gas jet atomizing arrangement, in which the liquid is supplied together with a compressed, inert gas.

Figure 1A:
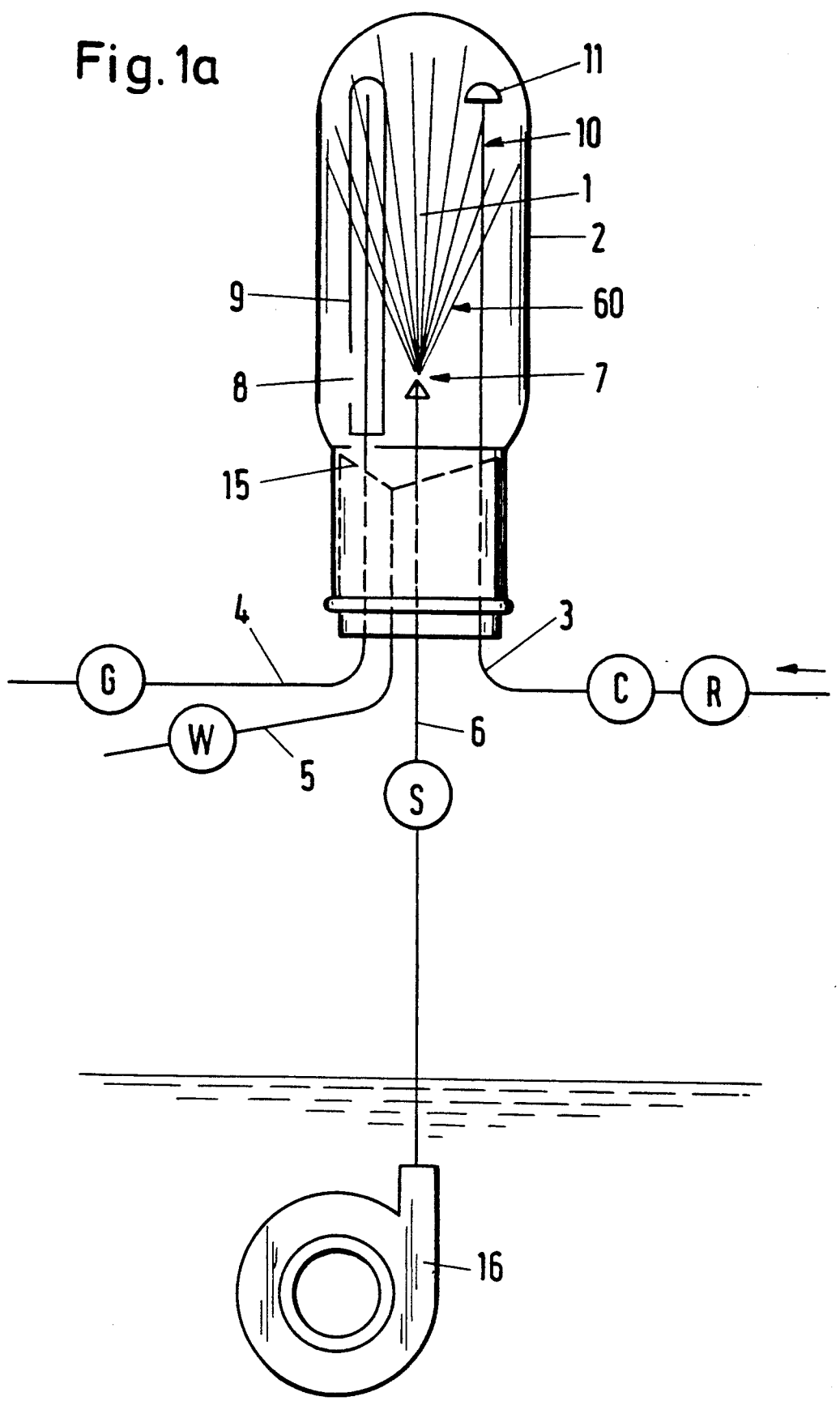

FIG. 1a shows such an alternative embodiment including a pump 16 located beneath the liquid level. The pump 16 is directly connected to the chamber 1 via a magnetic shut-off valve S. The extraction chamber of FIG. 1a corresponds to the extraction chamber in FIG. 1.

Figure 2:
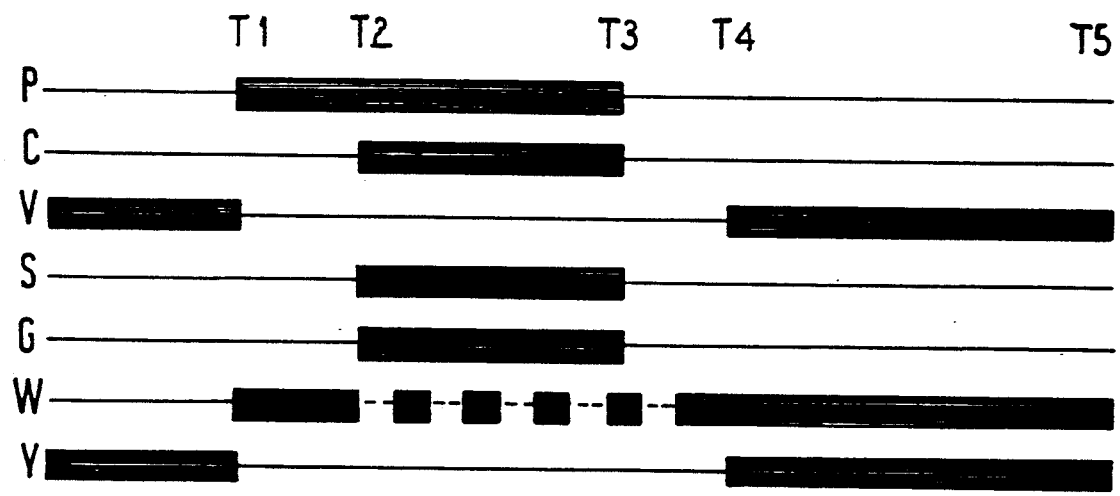

FIG. 2 illustrates a control diagram for the valves C, G, P, S, V, W, and Y provided in the apparatus of the invention. No control is necessary for the pressure-reducing valve R. The widened portions of the lines in the diagram indicate the chronological durations wherein the corresponding valves are open. The admission of pressurized gas into the specimen chamber is controlled via the compressed gas valve P. The admission of carrier gas into the extraction chamber is controlled via the carrier gas admission valve C. The pressure-relief valve V releases over-pressure in the specimen chamber. The magnetic shut-off valve S selectively regulates flow between the specimen chamber and the extraction chamber. The gas discharge valve G controls the discharge of gas from the extraction chamber. The liquid discharge valve W controls the discharge of liquid from the extraction chamber. The pressure valve Y is disposed in the floor of the specimen chamber, and automatically closes when the specimen chamber is pressurized. The pressure valve Y and the pressure-relieving valve V are first opened, and liquid can enter into the specimen chamber. At time T1, the pressure discharge valve is closed and pressure is delivered into the specimen chamber via the valve P, so that the pressure valve Y closes. The liquid discharge valve W is opened at time T1 in order to allow residual liquid to pass out of the extraction chamber. At time T2, the valve S is opened, allowing liquid to pass from the specimen space to the extraction chamber. At the same time, the liquid discharge valve W is closed, but is subsequently periodically opened in order to eliminate excess liquid; as described hereinabove, however, a predetermined liquid level is always maintained in the sump over the liquid discharge. Simultaneously with the valve S, the carrier gas admission valve C and the gas discharge valve G also opened. When the spraying process is ended at time T3, the valves P, C, S, and G close. The liquid discharge valve W is subsequently briefly opened, after which the pressure discharge valve V is opened at time T4 in order to relieve the pressure in the specimen chamber, whereupon the pressure valve Y at the floor of the specimen chamber opens and admits new liquid into the specimen chamber. The specimen-taking cycle ends at time T5.

In an alternative embodiment (not shown), the liquid level in the sump can be maintained by the use of a U-shaped pipe. The pipe projects into the cylinder, and has a piston placed thereon. The pipe can be provided at the liquid discharge, so that no liquid is eliminated before a corresponding liquid level is reached.

It is also possible to combine the liquid discharge with the vapor discharge, whereby the gas is separated from the liquid in a separate cylinder. In such an arrangement, there is no risk that vapors will be lost via the liquid discharge. A liquid/vapor separating cylinder is then required in addition to the vapor cylinder. The liquid is discharged through a U-shaped pipe that is directly connected to the separating cylinder and has a piston at its lowest level.

The gas separated from the liquid is supplied to an automatic specimen-extraction device and the organic and inorganic substances are collected and enriched in a collecting device. After being collected, the compounds are desorbed and supplied to a gas chromatograph.

Figure 3:
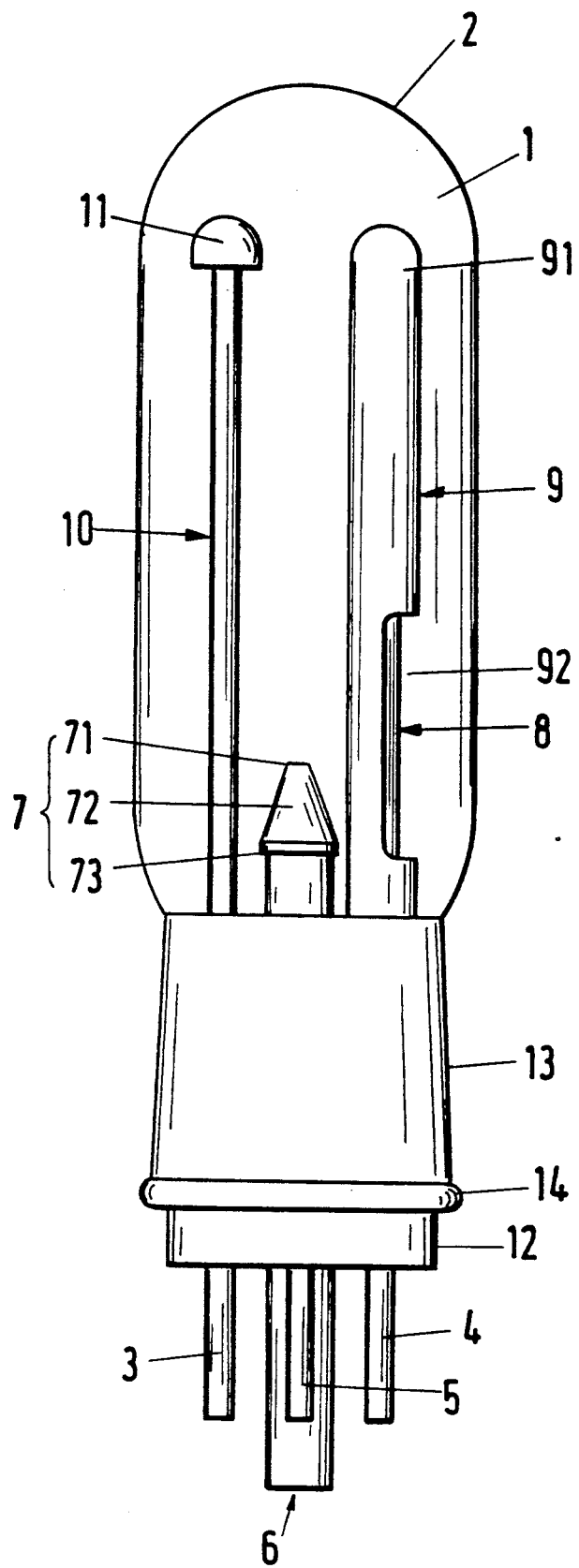

FIG. 3 illustrates a view of the extraction chamber of the apparatus of the invention. The extraction chamber includes a metallic or glass cylinder 2 having a cleaned and polished inside surface. The cylinder 2 is essentially a cylindrical body that terminates in a hemispherical upper dome. At its lower end, the cylinder 2 tapers to form a neck 13 having an adjoining collar 14. The cylinder 2 is closed with a plug 12 that can be pushed into the neck 13. The plug 12 also accepts the various admission and discharge components. The gas delivery conduit 3 for the carrier gas extends through the plug 12, and discharges into an admission tube 10 that is provided at its upper end with a protective cap 11. The cap 11 prevents liquid sprayed into the cylinder 2 from entering the admission tube 10. The liquid admission conduit 6 also passes through the plug 12, and discharges into a liquid injection arrangement 7 that is shown, in this embodiment, as a nozzle. The nozzle includes an outlet aperture 71 that is connected to the liquid admission conduit 6 via a frustoconical section 72 and a connecting collar 73. The liquid discharge conduit 5 also passes through the plug 12. Together with the liquid vapor, the carrier gas is supplied to a gas discharge pipe 8 that is provided with a protective sheath 9. The protective sheath 9 has a hemispherical termination 91 at its upper end. An opening 92 provided in the protective sheath 9 allows the carrier gas and the liquid vapor to proceed into the pipe 8. The opening 92 faces away from the liquid jet and is directed toward the inside wall of the cylinder 2, in order to reduce the risk of liquid contamination of the gaseous discharge.

Figure 4:
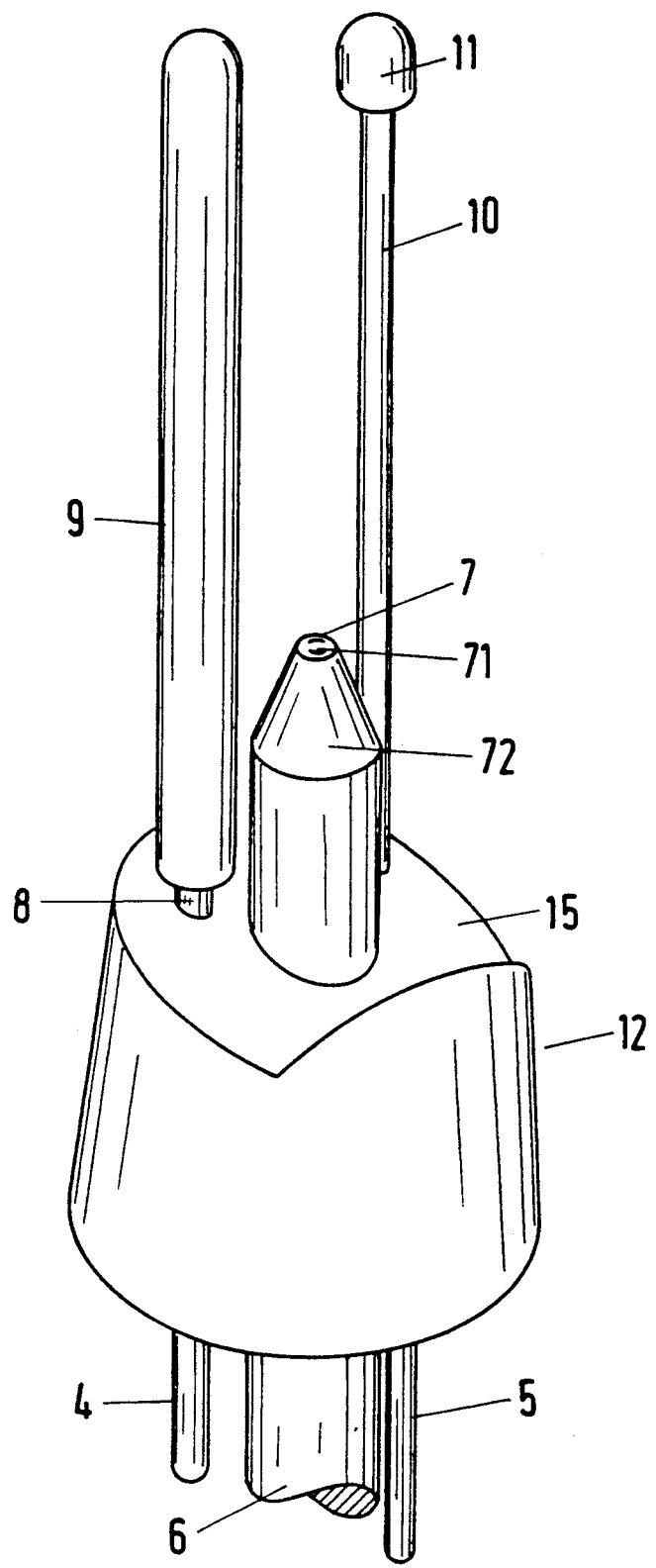

FIG. 4 shows a detailed view of the admission and discharge components for liquid and carrier gas on the plug 12. At its upper side, the plug is provided with a sump 15 in communication with the liquid discharge conduit 5. The admission opening of the liquid discharge conduit 5 is disposed at the lowest-lying point of the chamber 1. The liquid admission conduit 6 is centrally located in the plug 12. In the illustrated embodiment, the conduit 6 is directly connected to a liquid injection arrangement 7, here provided as a nozzle. The nozzle aperture 71 is situated at the upper end of the frustoconical section 72, so that the liquid entering through the conduit 6 is sprayed up in a vertical direction. The admission tube 10 and the discharge tube 8 project through the plug 12, and are of approximately equal length. The upper opening of the tube 10 is protected against liquid contamination by a protective cap 11. The gas discharge tube 8 is substantially completely surrounded by a protective sheath 9 extending above the plug 12.

Figure 5:
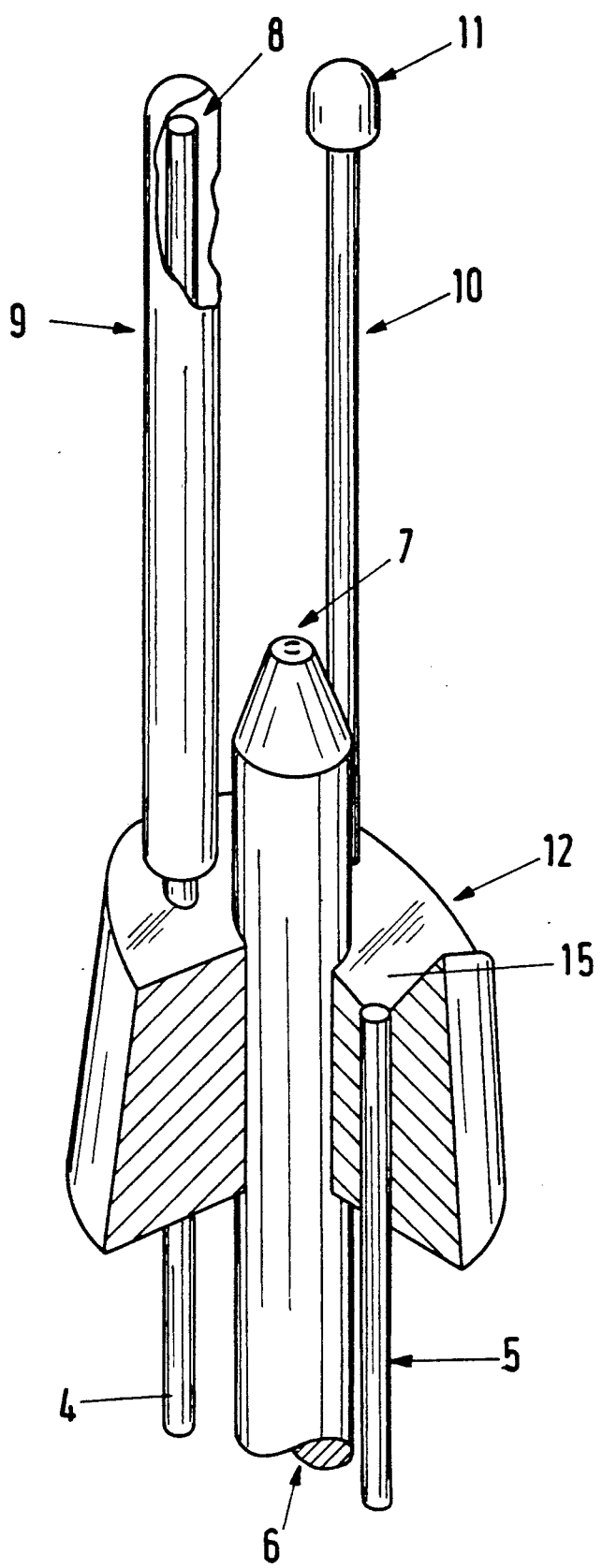

FIG. 5 shows a view of the arrangement of the admission and discharge conduits similar to that of FIG. 4, wherein the plug 12 and the protective cladding 9 are partially broken-away. The liquid discharge conduit 5 passes through the plug 12 as a pipe, and opens into the sump 15 at the surface of the plug. The protective sheath 9 surrounds the gas discharge tube 8 such that the opening for the carrier gas situated at the upper end of the gas discharge tube 8 is protected from liquid, but fully exposed to carrier gas and liquid vapor.

Figure 6:
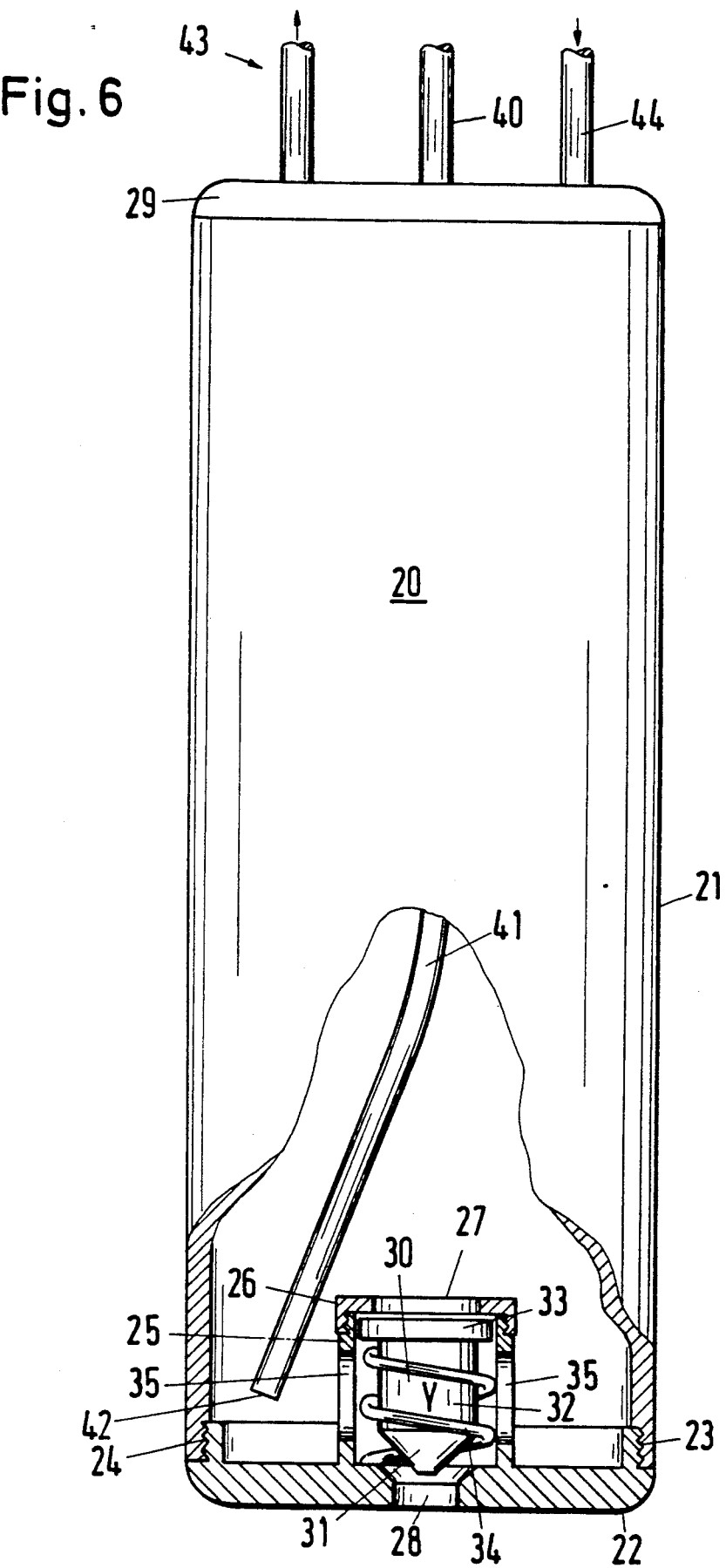

FIG. 6 shows an embodiment of the specimen chamber of the apparatus of the invention, wherein the lower region of the specimen chamber 20 is shown partially broken-away. The specimen chamber 20 includes a cylindrical pressure housing 21 that is closed with a cover 29. The cover 29 may, for example, be screwed to the housing 21. A compressed gas conduit 44 passes through the cover, and admits gas to pressurize the specimen chamber 20. A pressure-reducing line 43 through which pressure within the specimen chamber 20 can be relieved, as well as the lead 40 providing a connection to the extraction chamber 1, also pass through the cover 29. The lead 40 projects into the inside of the housing 21 to a point adjacent a specimen chamber floor 22. An obtuse-angle knee 41 is provided in the lead 40, so that the lead 40 clears the pressure valve Y. The lead 40 has an admission aperture 42 disposed adjacent the floor 22 next to the pressure valve Y. The pressure housing 21 has a lower end that is provided with an inside thread 23, so that the floor 22 (provided with a corresponding outside thread 24) can be screwed to the pressure housing 21. The floor 22 has a central floor opening 28 that diverges conically toward the inside of the housing. A valve housing 25 that terminates in a screwed-on closure plate 26 is provided around the floor opening 28. The closure plate 26 includes an opening 27. A valve body 30 having a cylindrical portion 32 is surrounded by a helical spring 34 is disposed inside the hollow tube 25. The helical spring biases the conically tapering end section 31 of the valve body 30 away from the floor opening 28, so that liquid can flow into the specimen chamber 20 through the floor opening 28 when the spring is not loaded (i.e., when the chamber is not pressurized). The cylinder 32 is provided with a head section 33. When the helical spring 34 is compressed during pressurization of the chamber 20, the end section 31 closes the floor opening 28, and liquid delivery is cut off.

Figure 6A:
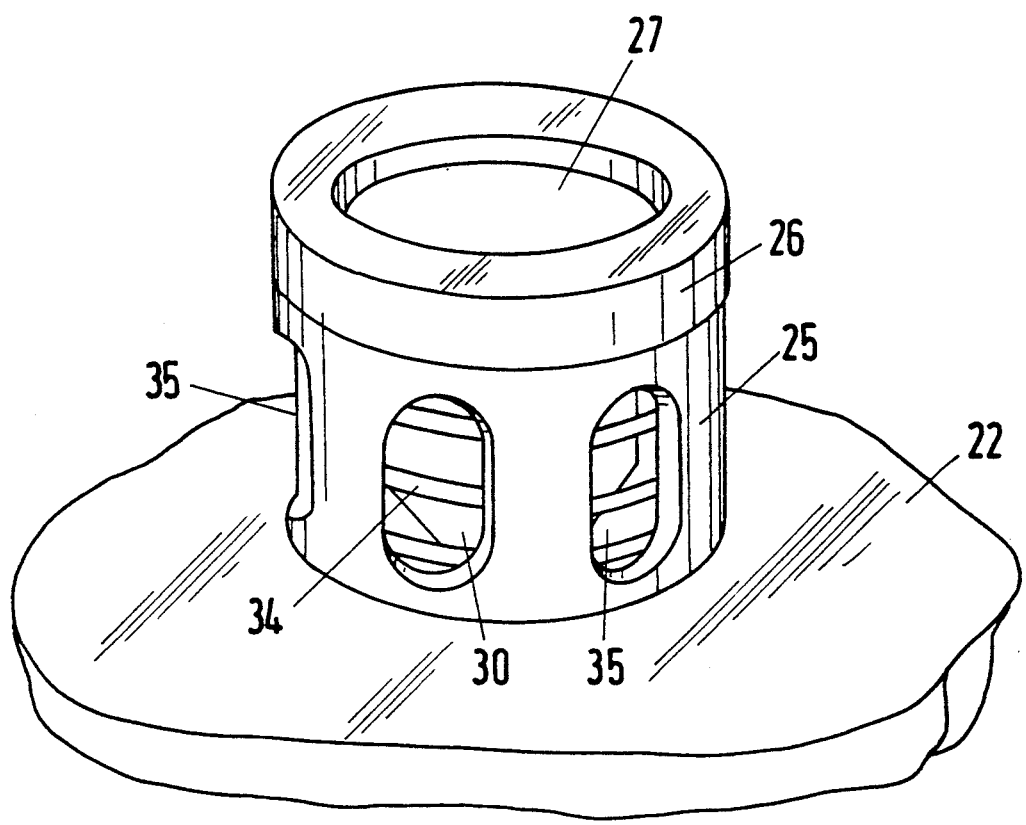

FIG. 6a is a schematic view of the pressure valve of FIG. 6. The valve housing 25 is provided with a plurality of lateral openings 35 that facilitate the flow of liquid into the specimen chamber 20. The lateral openings 35 are regularly spaced from one another, and extend over substantially the entire height of the housing wall.

Figure 7A:
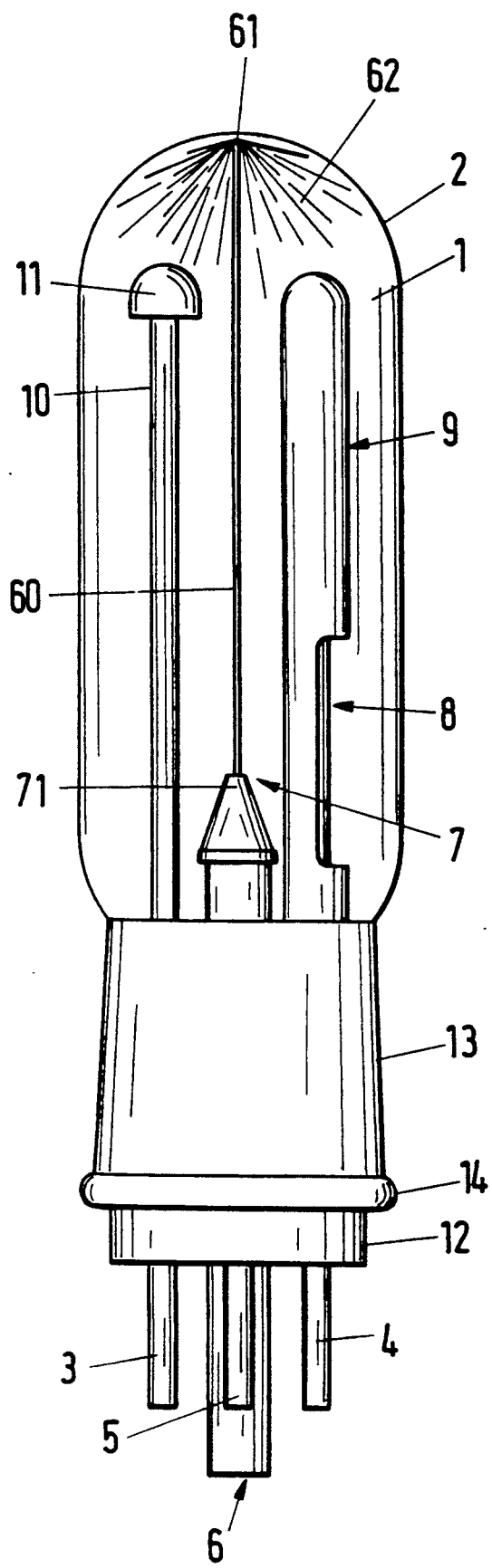

FIG. 7a illustrates the operation of an extraction chamber 1 that structurally corresponds to the extraction chamber set forth in conjunction with FIG. 3. A focused liquid jet 60 enters into the cylinder 2 through the nozzle aperture 71 of the injection arrangement 7. The liquid jet 60 is atomized into droplets 62 at a point 61, the point of incidence of the jet 60 with the inside of the upper end of the cylinder 2. The droplets are then largely radially-symmetrically distributed toward the inside of the cylinder. The atomization of the liquid jet 60 provides a large contact surface area between liquid and gas, so that the desired distribution equilibrium can be established in a short time.

Figure 7B:
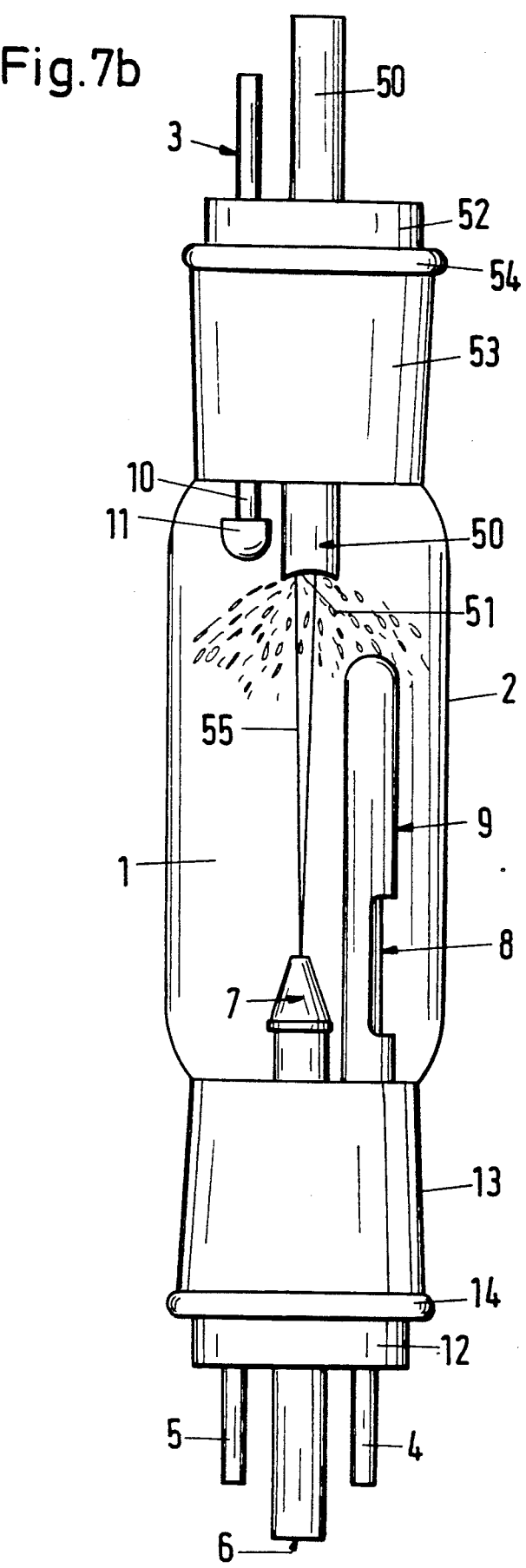

FIG. 7b illustrates an embodiment of the extraction chamber wherein an alternative deflection arrangement for breaking up the liquid jet is provided. In this extraction chamber 1, the cylinder 2 has both its lower and its upper end provided with a respective neck (13, 53) with a collar (14, 54) that is closed with a corresponding plug (12, 52). The liquid discharge conduit 5, the specimen admission conduit 6 and the discharge conduit 4 for the carrier gas pass through the lower plug 12. The admission conduit 3 for carrier gas passes through the upper plug 52, and discharges into an admission tube 10 that projects into the cylinder 2. The mouth of the admission tube 10 is closed with a protective cap 11. A rod 50 projects beyond the admission tube 10 into the inside of the cylinder 2, and passes centrally through the plug 52. The inwardly directed end face 51 of the rod 50 is concavely arced. A liquid jet 55 emerges from the injection arrangement 7 and strikes the concave end face 51 of the rod 50. The jet 55 is atomized and the resultant liquid droplets are deflected such that because of the curvature of the end face 51, liquid droplets cannot reach the admission tube 10. The droplets again offer the above-described large contact surface between liquid and gas, so that carrier gas and liquid vapor can be extracted through the gas discharge tube 8.

Figure 7C:
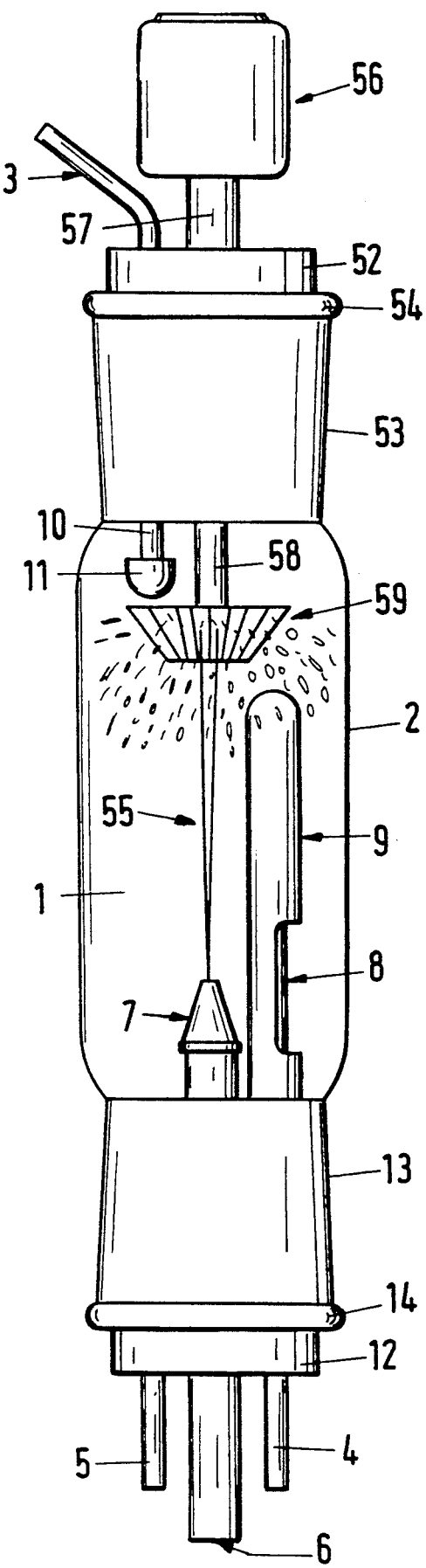

FIG. 7c shows another alternative embodiment of the extraction chamber, wherein a motor-driven rotatable deflector 59 is provided. Admission and discharge conduits for liquid and carrier gas are arranged as in the embodiment of FIG. 7b; however, the admission conduit 3 for the carrier gas is provided with an elbow. A protective pipe 57 surrounds a shaft of a motor 56, and projects through the upper plug 52. The motor 56 rotates the deflector 59 via a shaft 58. The deflector 59 resembles a truncated cone, and may be provided with ribs, projections, or lamellae that extend along the surface of the truncated cone. The deflector 59 is conically convergent in a downward direction. The planar upper surface of the deflector extends beyond the opening of the admission tube 10 with the protective cap 11. The liquid jet 55 sprayed from the injection arrangement 7 strikes the lower surface of the deflector 59 and is atomized. The rotation of the deflector 59 and of the ribs or projections arranged thereon assist in the formation of liquid droplets. The liquid droplets are diverted such that they are predominately downwardly directed, and do not enter the admission pipe 10. Carrier gas and liquid vapor as set forth above, can be extracted through the discharge tube 8.

Figure 8:
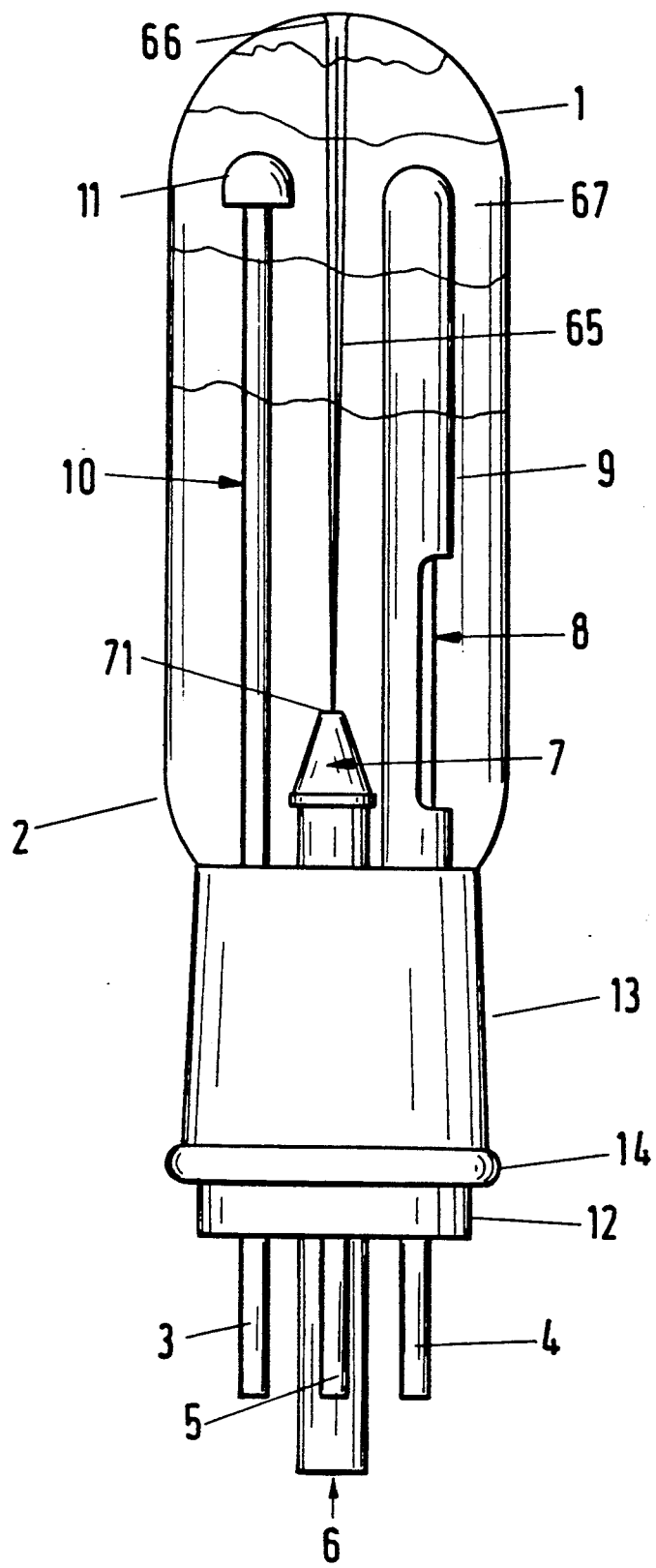

FIG. 8 illustrates an extraction chamber similar to that shown in the embodiment of FIG. 7a, except that the liquid jet 65 emerges from the discharge opening 71 of the injection arrangement 7 at a lower speed. The low-speed stream does not break up when it strikes the surface 66, but rather flows downwardly along the inside walls of the cylinder 2 as a thin liquid film 67. The formation of the film again establishes a large contact surface area between liquid and gas. After extraction of a vapor sample, the liquid is eliminated via the liquid discharge conduit 5.

Figure 9:
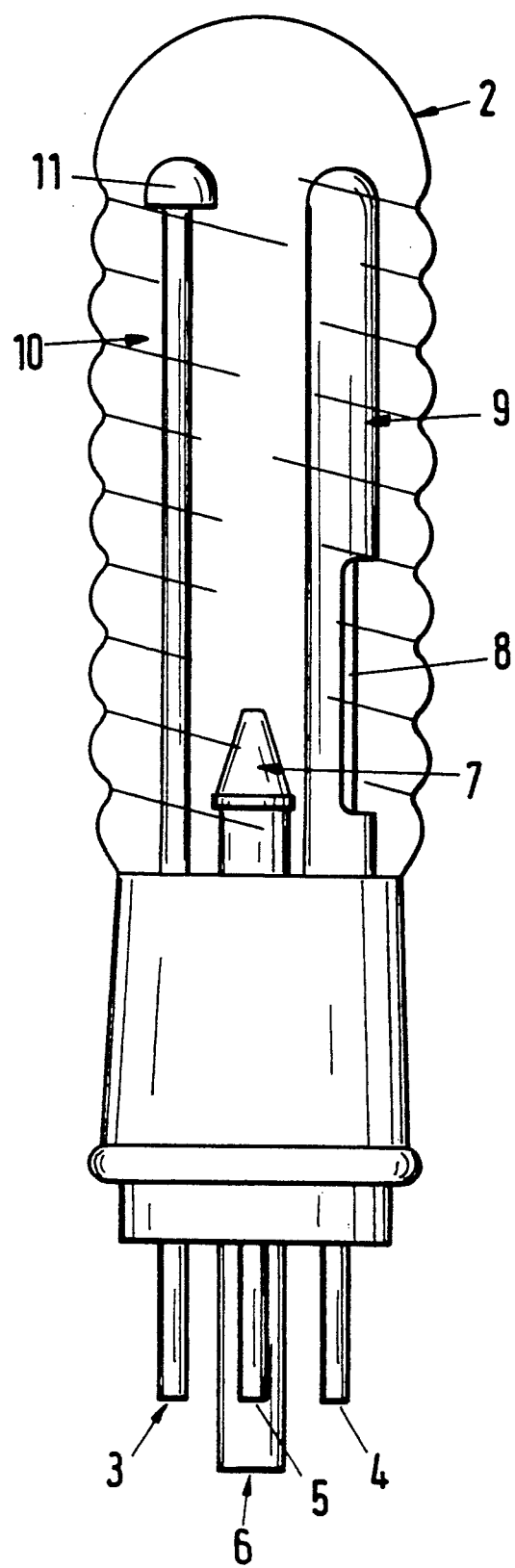

FIG. 9 shows an embodiment of the invention wherein the cylinder 2 has side walls that have a "wave-shaped" profile. When the liquid, (as in the embodiment of FIG. 8) flows downwardly over the walls as a thin film, the surface is larger than that of a similar film on a smooth-walled cylinder. The arrangement of admission and discharge conduits for liquid and carrier gas, as well as the injection arrangement correspond to those in the embodiment of FIG. 8.

Figure 10:
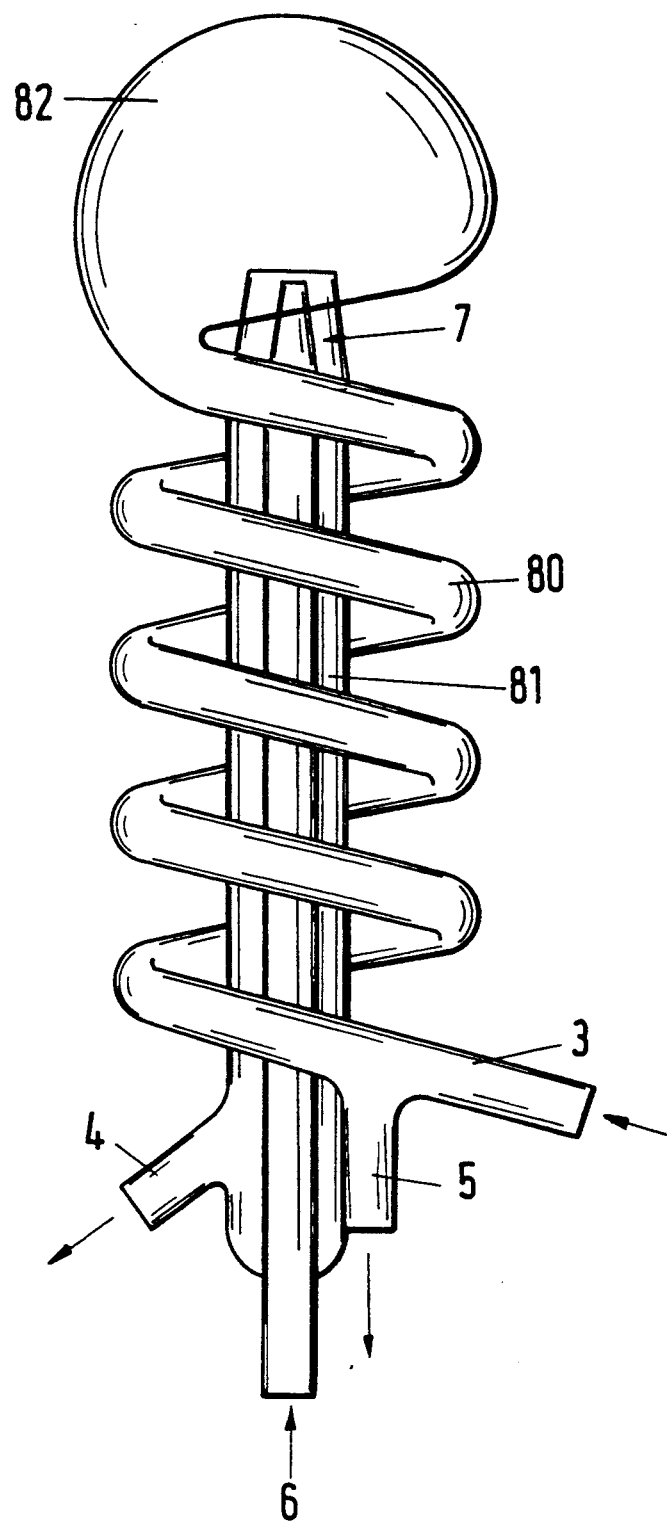

FIG. 10 shows an extraction chamber that is provided as a generally helical pipe 80, in contrast with the generally cylindrical chambers of the preceding embodiments. The liquid admission conduit 6 extends along the center axis of the helix, and terminates in an injection arrangement 7. The liquid is sprayed into a spray chamber 82, and flows down along the helical pipe 80. Carrier gas is introduced at the lower end of the helix via an admission conduit 3, and moves upwardly together with the liquid vapor, in a "counter-current" flow with respect to the liquid. Gas is then eliminated via the gas discharge conduit 4 through a pipe 81 placed around the liquid admission 6. The liquid flowing down along the inside walls of the helical pipe 80 is eliminated via the liquid discharge conduit 5 that is disposed at the underside of the last helical turn.

Figure 11:
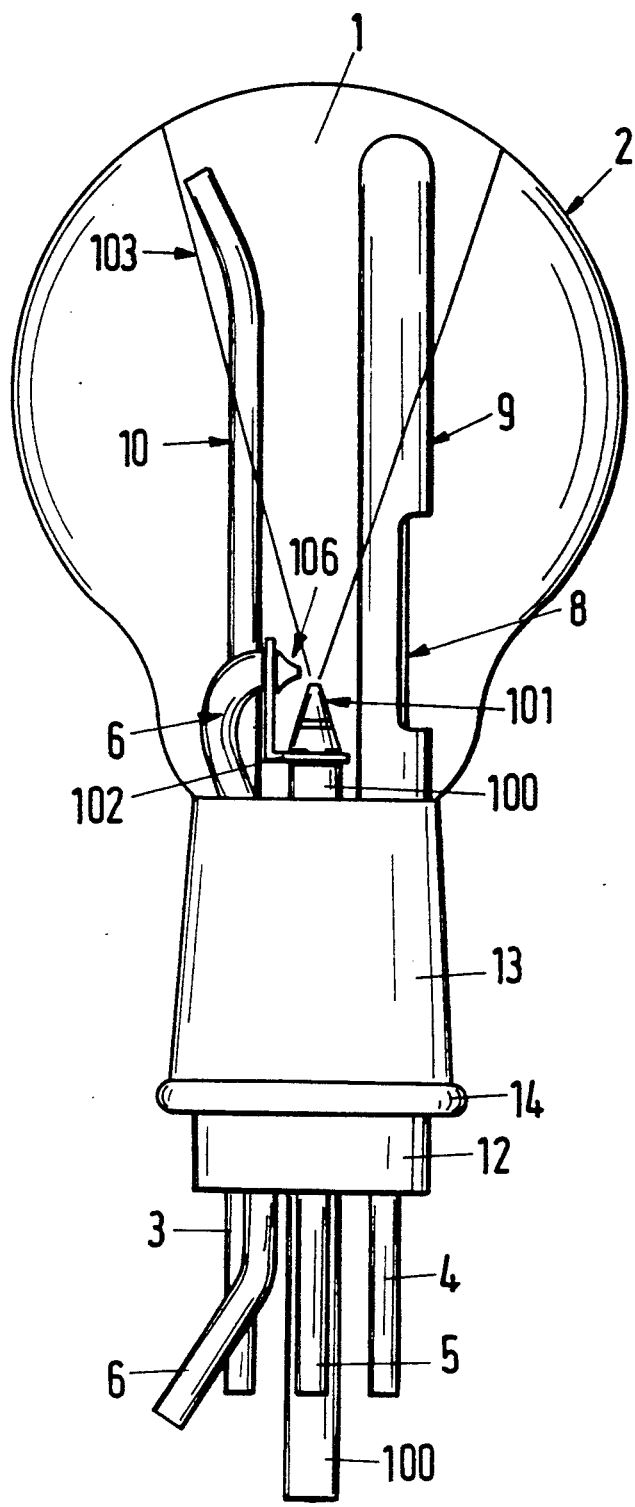

FIG. 11 shows an extraction chamber 1 that is configured as an essentially spherical or pear-shaped chamber 2. This chamber 2 is provided with a neck 13 having a collar 14, and is closed by a plug 12. The admission conduit 3 for carrier gas passes through the plug, and the admission tube 10 has an acute-angle bend at its upper end. The discharge conduit 4 for carrier gas is connected to the gas discharge tube 8 that is provided with a protective sheath 9. A pressurized gas conduit 100 passes centrally through the plug 12. The pressurized gas conduit terminates in a gas nozzle 101 having a vertical spraying direction. The liquid admission conduit 6 likewise passes through the plug, and is provided with a curved or "goose neck" portion. The liquid admission conduit 6 terminates in a liquid injection nozzle 106 having a horizontal discharge direction. An angle brace 102 maintains the liquid nozzle 106 and the gas nozzle 101 at a precise right angle relative to one another. Liquid emerging from the nozzle 106 is atomized and entrained by the compressed gas emerging from the gas nozzle 101. Such a gas jet atomizing arrangement generates a dynamic vacuum in accordance with the Bernoulli principle. This method produces the smallest liquid droplets, and thus the largest effective liquid surface. Liquid and air or an inert gas cross in the nozzle system 106, 101 perpendicularly aligned relative to one another, and a broadly fanned spray jet 103 results.

Figure 12:
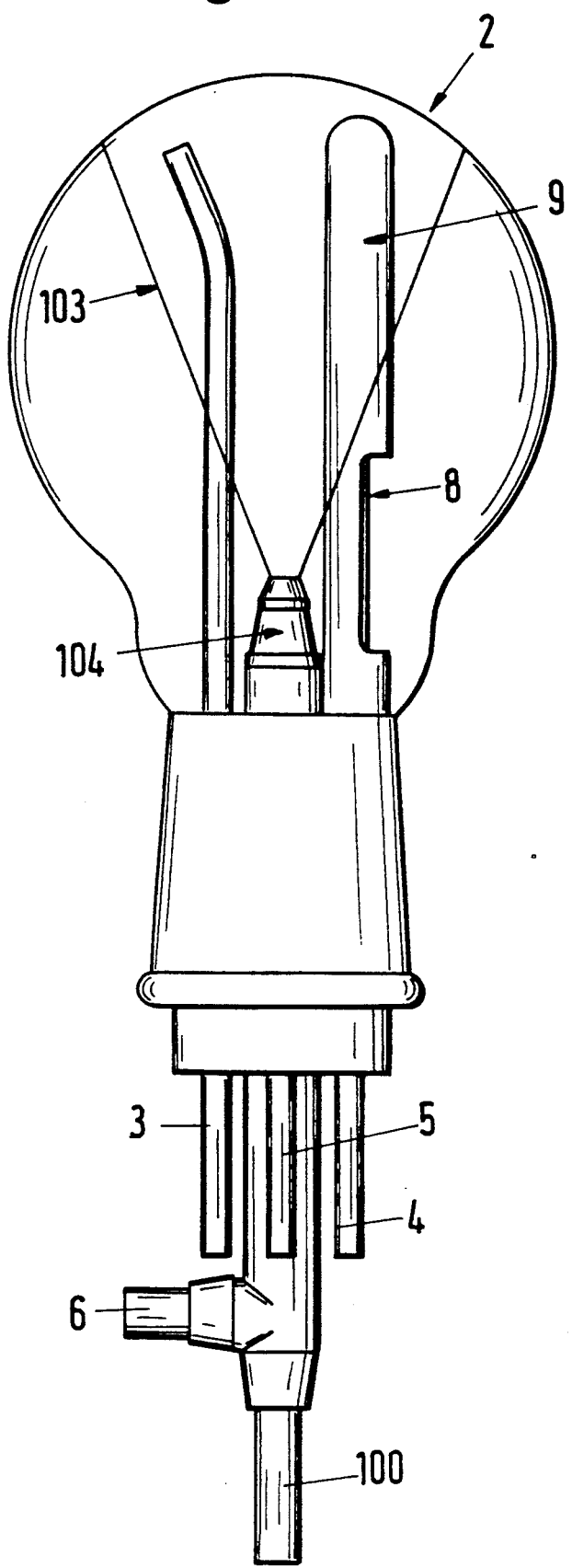

The embodiment of FIG. 12 operates according to the same principle. The pressurized gas conduit 100 and the liquid admission conduit 6 are brought together, and liquid and gas are mixed in a liquid spraying nozzle 104 including concentric tubes. The atomizer gas can be the carrier gas, so that an admission conduit 3 for carrier gas can be eliminated.

Figure 13:
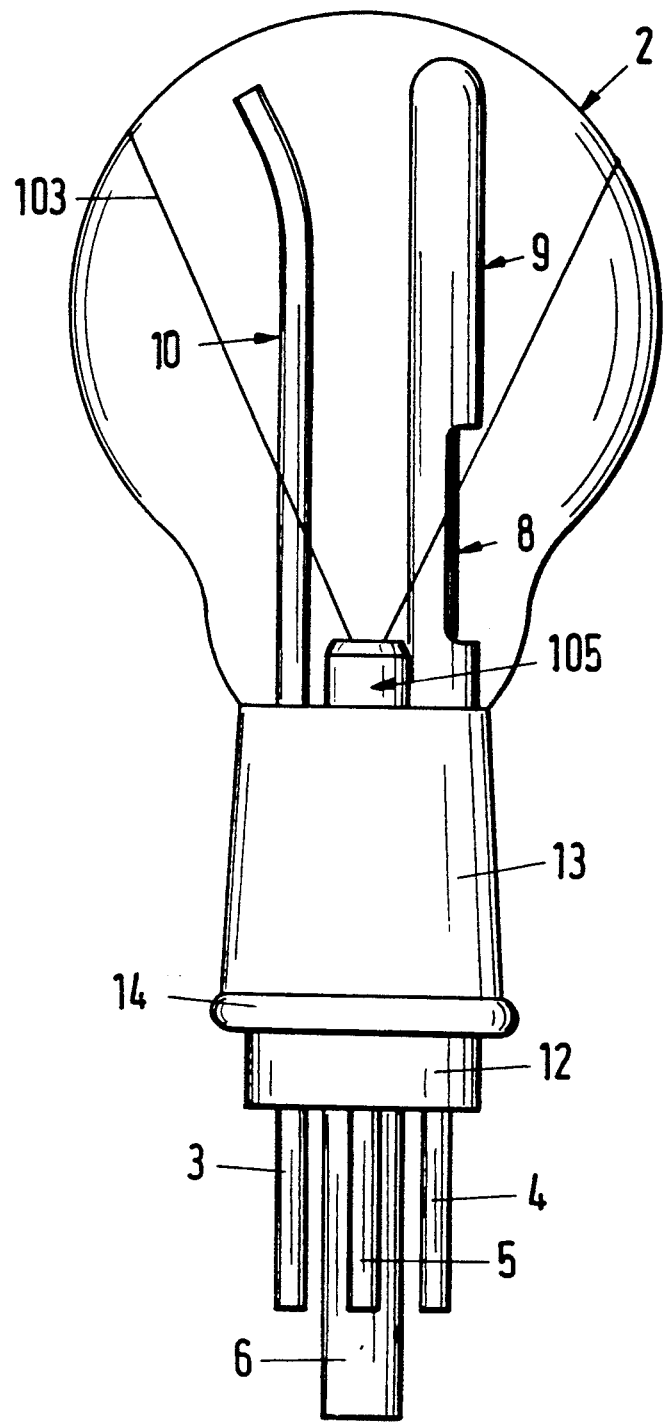

In the embodiment of FIG. 13, a liquid injection valve 105 is provided for spraying the liquid. The liquid injection valve 105 opens at a defined pressure, producing a liquid film in the form of a spray cone. This embodiment is particularly suitable when the liquid is pumped from a liquid specimen chamber. Since the injection valve is provided with a constant liquid stream, the liquid film becomes thinner as it moves away from the liquid injection valve 105, and breaks up into small droplets. The break up point, or point of de-aggregation, is dependent on the aperture angle of the spray cone, and on the surface tension of the liquid. The valve 105 can be adjustable (for example, with a selectively adjustable spring mechanism), so that the thickness of the liquid film, the discharge speed, the point of de-aggregation and the pressure at which the valve opens, can be selectively set.

In each of the embodiments of the extraction chamber, additional admission and discharge conduits for water or other cleaning fluid can be provided to rinse the inside of the chamber. The cylinder of the extraction chamber is preferably composed of glass or metal, and the plugs are preferably composed of polytetrafluorethylene.

Although the present invention has been described with reference to a specific embodiment, those of skill in the art will recognize that changes may be made thereto without departing from the scope and spirit of the invention as set forth in the appended claims.

I claim as my invention:

1. A method for extracting volatile substances from a liquid into the gas phase in which the extracted gaseous substances are withdrawn from a headspace formed in an extraction chamber, comprising the following steps:

spraying the liquid comprising the volatile substance(s) into the headspace in such a manner that droplets of liquid with extremely small radii of curvature are created;

passing a carrier gas through the extraction chamber, where the gaseous substances are withdrawn from the droplets of liquid by the carrier gas for withdrawing the gaseous substance(s) from the droplets of liquid due to an increase in vapor pressure, and where the vapor pressure is increased as a result of the extremely small radii of curvature of the droplets of liquid; and transferring the gaseous substance(s) withdrawn from the extraction chamber to an analytical device.

2. A method according to claim 1, wherein said step of spraying said liquid comprises:
pressurizing said liquid; and
spraying said pressurized liquid into said extraction chamber.

3. A method according to claim 1, wherein said step of spraying said liquid comprises:
pressurizing said liquid with a pressurized gas; and
spraying said pressurizing liquid into said extraction chamber.

4. A method according to claim 1, further comprising the step of collecting a predetermined amount of liquid before said step of spraying said liquid.

5. A method according to claim 1, further comprising the step of maintaining liquid within said extraction chamber at a level below said head space.

6. An apparatus for extracting volatile substances from a vaporized liquid, said apparatus comprising the following: an extraction chamber in fluid communication with a liquid specimen source; liquid injection means, extending into said extraction chamber, for spraying liquid from said liquid specimen source into said extraction chamber to form droplets of liquid with extremely small radii of curvature; and carrier gas inlet means, connected to said extraction chamber, for passing a carrier gas through said extraction chamber for withdrawing gaseous substances from the droplets of liquid, where the gaseous substances are withdrawn from the droplets of liquid by the carrier gas due to an increase in vapor pressure, and where the vapor pressure is increased as a result of the extremely small radii of curvature of the droplets of liquid.

7. An apparatus according to claim 6, wherein said liquid injection means comprises an injection valve.

8. An appartus according to claim 6, wherein said liquid injection means comprises a nozzle.

9. An apparatus according to claim 6, wherein said liquid injection means comprises a gas jet atomizer assembly 10. An apparatus according to claim 6, wherein said liquid injection means comprises an injection valve capable of generating a conical spray jacket, said injection valve including spring-biased means for varying the spray aperture of said injection valve.

11. An apparatus according to claim 6, further comprising specimen chamber means for collecting liquid from said liquid specimen source.

12. An apparatus according to claim 6, wherein said vapor extraction chamber comprises an outer wall having a wave-shaped profile.

13. An apparatus according to claim 6, wherein said extraction chamber comprises a generally helical portion.

14. An apparatus according to claim 6, further comprising deflecting means, disposed within said extraction chamber, for atomizing said liquid sprayed from said liquid injection means.

15. An apparatus according to claim 14, wherein said deflecting means comprises a rod.

16. An apparatus according to claim 14, wherein said deflecting means comprises a rotable deflector.

17. An apparatus according to claim 6, wherein said carrier gas inlet means comprises:
a carrier gas supply tube in comunication with a carrier gas source, said carrier gas supply tube extending into said extraction chamber, and having a terminal end disposed in said extraction chamber; and a protective cap disposed on said terminal end of said carrier gas supply tube.

18. An apparatus according to claim 6, further comprising gas discharge mean, adjacent said extraction chamber, for facilitating the removal of vaporized liquid from the extraction chamber.

19. An Apparatus according to claim 18, wherein said gas discharge means comprises:
a gas discharge tube extending into said extraction chamber; a protective sheath surrounding said gas discharge tube and extending from a floor of said extraction chamber; and a lateral opening disposed at a lower end of said protective sheath.

* * * * *